United States Patent [19]

Simon et al.

[11] Patent Number: 4,857,573

[45] Date of Patent: Aug. 15, 1989

[54] PLASTIC MATERIAL CONTAINING A TETRACARBOXYLIC ACID TETRAESTER-PLASTICIZER

[75] Inventors: Wilhelm Simon, Zurich, Switzerland; Urs Oesch, Holliston, Mass.

[73] Assignee: Firma Willi Moller, Zurich, Switzerland

[21] Appl. No.: 105,626

[22] Filed: Oct. 6, 1987

[30] Foreign Application Priority Data

Oct. 7, 1986 [CH] Switzerland .......................... 4007/86

[51] Int. Cl.[4] .............................................. C08K 5/09
[52] U.S. Cl. ..................................... 524/291; 524/292
[58] Field of Search ................................. 524/291, 292

[56] References Cited

U.S. PATENT DOCUMENTS

| | | |
|---|---|---|
| 3,293,267 | 12/1966 | McCracken et al. . |
| 3,332,964 | 7/1967 | McCracken et al. . |
| 3,389,168 | 6/1968 | Hirzy . |
| 4,309,524 | 1/1982 | Huemmer et al. . |
| 4,608,149 | 8/1986 | Daniel et al. . |

FOREIGN PATENT DOCUMENTS 5974144 10/1982 Japan .

OTHER PUBLICATIONS

Chem. Abstracts #106:55878e, Oesch et al., 1986.

*Primary Examiner*—Joseph L. Schofer
*Assistant Examiner*—Peter D. Mulcahy
*Attorney, Agent, or Firm*—Seidel, Gonda, Lavorgna & Monaco

[57] ABSTRACT

Plastic material compositions which comprise a plastic material matrix containing a benzhydrol-tetracarboxylic acid tetraester as a plasticizer are disclosed. The plasticizer is firmly anchored within the matrix such that migration of the plasticizer, and any other optionally present matrix components having a molecular weight of at least 100, are inhibited within the matrix. The plasticizer and matrix components are inhibited from eluting from the matrix when the matrix is brought in intimate contact with a liquid or solid material. These compositions are particularly useful as shaped bodies possessing highly elastic and adhesive characteristics.

21 Claims, No Drawings

PLASTIC MATERIAL CONTAINING A TETRACARBOXYLIC ACID TETRAESTER-PLASTICIZER

BACKGROUND OF THE INVENTION

The present invention is concerned with plastic compositions which contain a tetracarboxylic acid tetraester-plasticizer. Said plasticizer is a benzhydrol-tetracarboxylic acid tetraester in which the esterifying alcohol components are alkanols, alkenols or alkinols and said alcohol components comprise 4–24 carbon atoms.

Said tetracarboxylic acid tetraester is rather firmly anchored in the matrix of plastic material so that even after extended storage periods no migration of the plasticizer in the matrix of the plastic material occurs. Due to the firm anchoring of the plasticizer in the matrix of the plastic material said plasticizer also does not migrate into solid materials or liquids which are kept in contact with the inventive plastic compositions.

If the inventive plastic compositions comprise in addition to the plasticizer at least one further component having a not too low molecular weight, e.g. a molecular weight of about 100 or higher, then also said component is anchored in the matrix of the plastic material through the benzhydrol-tetracarboxylic acid tetraester. Said further component can e.g. be an ion sensitive component and corresponding ion sensitive parts accordingly have a very long life period. Contrary to this, the benzophenone tetracarboxylic acid tetraester of the inventive plastic compositions do not inhibit the migration of small ions like cations of alkaline earth metals or alkali metals or the anions of halides or carbonate anions. so that corresponding ion selective parts are well suited for the determination of the concentration of the corresponding anions or cations in liquid media.

Inventive plastic materials which contain high quantities of the tetracarboxylic acid tetraester-plasticizer, like 15–90 parts by weight of said plasticizer per 10 parts by weight of the plastic components, have high elasticity and high adhesive characteristics.

DESCRIPTION OF THE PRIOR ART

It is well known in the art to add to plastic materials plasticizers in order to make plastic materials which are brittle or not sufficiently flexible usable in their desired fields of application.

In the U.S. Pat. No. 3,389,168 of J. W. Hirzy there are described diallyl-benzophenone-tetracarboxylates which have the following formula

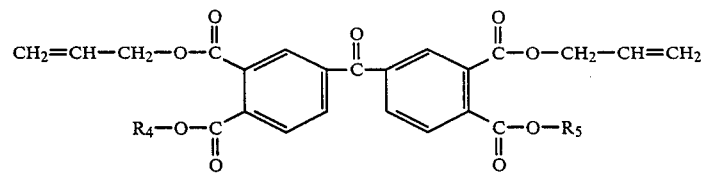

wherein $R_4$ and $R_5$ are selected from the group comprising allyl, alkyl having 1–18 carbon atoms and cycloalkyl having 6–18 carbon atoms. Said benzophenone tetracarboxylates are used as plasticizers and crosslinking agents for halogen containing vinyl polymers, and according to the examples 16 and 17 of said patent per 100 parts by weight of polyvinylchloride 60 parts by weight of said plasticizer are used.

In the Japanese patent publication No. 59-74,144 of Kokai Tokkyo Koho and in the corresponding patent abstracts of Japan, volume 8, number 178 (C-33) [1615], Aug. 6, 1984, there are described plasticizers for vinylchloride polymers which have the following formula A

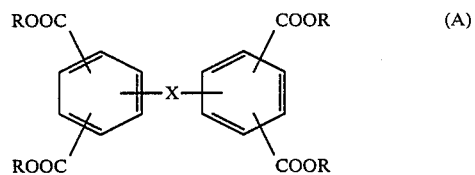

In said formula A, R is an aliphatic saturated hydrocarbon residue having 4–18 carbon atoms, X is oxygen, sulphur or a group of formula

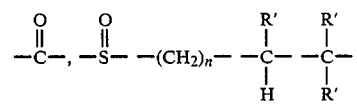

wherein
n is 1–6 and R' is a methyl group or trifluoromethyl group or

X has the meaning of certain bivalent organic residues which are bonded via an ether group to the two benzene nuclei. Per 100 parts by weight of vinylchloride resin 20–120 parts by weight, preferably 30–100 parts by weight of said tetracarboxylic acid tetraester of formula A are used. From said Japanese patent publication no reference can be taken that corresponding plasticized polyvinylchloride resins which contain high quantities of said plasticizers have good adherence or high elasticity. The plasticizers in question are benzophenone-tetracarboxylic acid tetraesters if in formula A the group X is —CO—.

In the not yet published U.S. patent application Ser. No. 914,390 of the applicant which is based on the Swiss patent application 4306/85-7 of Oct. 4, 1985, there are described shaped bodies of plastic material which have high elasticity and high adhesive characteristics. Said shaped bodies contain high quantities of a benzophenone-tetracarboxylic acid ester as a plastifying component, i.e. per 10 parts by weight of the plastic materials 7–90 parts by weight of said tetracarboxylic acid tetraester are used.

In the U.S. Pat. No. 3,293,267 there are described compounds having the following formula B

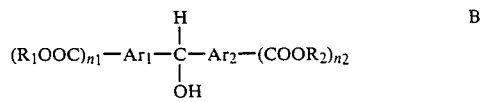

in which $Ar_1$ and $Ar_2$ are aromatic radicals or heteroaromatic radicals, for example phenyl radicals, biphenyl radicals or naphthyl radicals, and $R_1$ and $R_2$ are alkyl radicals having 1-19 carbon atoms and each of the symbols $n_1$ and $n_2$ is either the integer 1 or the integer 2.

If in said esters of formula B $n_1$ and $n_2$ are 2 and furthermore $Ar_1$ and $Ar_2$ are phenyl, then said esters are the benzhydrol-tetracarboxylic acid tetraesters. In column 1, lines 21-24 of said U.S. patent it is furthermore disclosed that the esters of formula B can be employed as intermediates in the preparation of plasticizers, plastics and fibres. No reference, however, can be taken from said U.S. patent that the esters of formula B themselves could be used as plasticizers.

Also in the U.S. Pat. No. 3,332,964 there are described tetracarboxylic acid tetraesters and in said esters the four carboxylate groups are bonded to the aromatic nuclei of diphenylmethane. Also in said patent there is stated that the esters in question can be employed as intermediates in the preparation of plasticizers, plastics and fibres. However, said patent cannot be taken as a reference that the esters themselves can be used as plasticizers.

It is furthermore well known in the art that ion selective membranes for the determination of the concentration of ions contain an ion selective component for the cation or anion to be determinated in a matrix of a plastic material. Said ion selective membranes usually contain as a further component a plasticizer in order to improve the properties of such ion selective membranes. Through said plasticizers for instance the stability of the electrodes is improved in which electrodes the ion sensitive part is the ion sensitive membrane in question and, furthermore, said plasticizers will also improve the selectivity and the response time of the electrodes and the ion sensitive members thereof respectively. Typical examples of plasticizers which until now had been used as component of ion sensitive members are esters of dicarboxylic acids, like for instance the diesters of phthalic acid, sebacic acid and adipic acid and, furthermore, as plasticizers of such ion selective parts there were also used aliphatic ethers and esters of the phosphoric acid like for instance mixed aromatic and aliphatic esters of the phosphoric acid.

The prior art ion selective electrodes which are equipped with an ion selective membrane containing the ion selective components embedded in a matrix of plastic material usually had only a rather short life period. The used plasticizers migrated in the matrix of the plastic material and they were eluted from the ion selective membranes by the sample solution when said electrodes were used for the determination of ion concentrations in liquid materials. Also migration problems occured when the corresponding ion selective membranes were used, applied to an electrode body of a different plastic material containing a different kind of plasticizer, because on one hand the plasticizer of the ion selective membranes migrated into said plastic material of the electrode body and also the plasticizer of the electrode body migrated into the plastic material of the ion sensitive membrane.

Also in many other fields of the application of plastic material problems are encountered because the plasticizer migrates in the plastic material that is often eluted by liquid materials which are in contact with said plastic material or because the plasticizer migrates into solid materials which are kept in intimate contact with the plastic material in question. Such problems are for instance to be encountered if a plastic foil is used as a carrier for layers of any other material, like e.g. layers of a light sensitive material.

It was the aim of the present invention to avoid the above stated problems of migration of the plasticizer in the matrix of a plastic material by using a certain class of tetracarboxylic acid tetraesters as plasticizers. Said new class of plasticizers are tetraesters of the benzhydrol-tetracarboxylic acid and said tetraesters also comprise esters of the above stated formula B which are already described in the U.S. Pat. No. 3,293,267.

DESCRIPTION OF THE PRESENT INVENTION

It was unexpectedly discovered that tetracarboxylic acid tetraester-plasticizers which are the corresponding tetraesters of the benzhydroltetracarboxylic acid were firmly anchored in a matrix of plastic material, so that the above explained migration problems of plasticizers in a plastic material can be avoided with said tetracarboxylic acid tetraesters which until now had not been used as plasticizers.

One object of the present invention accordingly is a plastic material containing a tetracarboxylic acid tetraester as plasticizer and wherein said tetracarboxylic acid tetraester-plasticizer is a benzhydrol-tetracarboxylic acid tetraester, in which the carboxylate group of said tetraester is bonded directly to the aromatic nuclei of the benzhydrol and in said tetraester-plasticizer the esterifying alcohol component is selected from the group comprising alkanols, alkenols and alkinols all of which have 4-24 carbon atoms, and furthermore the aromatic nuclei of the benzhydrol structure are either unsubstituted or substituted with not ionic substituents and the alcohol moieties of said tetraester are either unsubstituted or substituted with not ionic substituents.

Said benzhydrol-tetracarboxylic acid tetraester is anchored in the matrix of the plastic material so that a migration of said plasticizer in the plastic material is inhibited even during long storage periods and also a migration of the plasticizer from the plastic material into solid or liquid materials which contact the plastic material is avoided.

Preferred benzhydrol-tetracarboxylic acid tetraesters used as plasticizer in the inventive plastic compositions are corresponding tetraesters in which the alcohol components of said tetraester are derived from straight chain alcohols or from alcohols having not more than three branchings.

Preferably in said benzhydrol-tetracarboxylic acid tetraesters each of the two phenyl nuclei is substituted with two ester groups. Of said preferred group of benzhydrol-tetracarboxylic acid tetraesters the corresponding compounds are preferred in which in the two phenyl nuclei the position of the ester groups is identical with regard to the carbon atom of the phenyl nucleus to which the group of formula

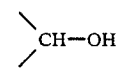

of the benzhydrol is bonded.

Of said preferred class of benzhydrol-tetracarboxylic acid tetraesters those are specially preferred, which correspond to the following formula I

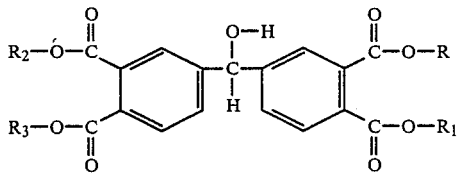

wherein each of the radicals
R, R₁, R₂ and R₃ is selected from the group comprising alkyl radicals having 4–22 carbon atoms, alkenyl radicals having 4–22 carbon atoms and alkynyl radicals having 4–22 carbon atoms.

Preferably in said benzhydroltetracarboxylic acid tetraesters of formula I each of the radicals R, R₁, R₂ and R₃ is selected from the group comprising alkyl radicals having 6–20 carbon atoms, alkenyl radicals having 6–20 carbon atoms and alkynyl radicals having 6–20 carbon atoms. Of said radicals the corresponding alkyl radicals having 6–20 carbon atoms are preferred, and furthermore preferably the radicals R, R₁, R₂ and R₃ are straight chain radicals or residues which have not more than three branchings.

Those benzhydrol-tetracarboxylic acid tetraesters which have a symmetric structure are specially preferred. Accordingly in the corresponding benzhydrol-tetracarboxylic acid tetraesters preferably the four ester forming groups have the same structure, and accordingly the preferred esters of formula I the radicals R, R₁, R₂ and R₃ are identical. Said tetraesters having a symmetric structure are also easier produced than corresponding esters having a not symmetric structure.

The benzhydrol-tetracarboxylic acid tetraester used as plasticizer in the inventive plastic compositions can be prepared by reducing the corresponding benzophenone-tetracarboxylic acid tetraester. For instance the preferred benzhydrol-tetracarboxylic acid tetraesters of the above stated formula I are preferably prepared by reducing a corresponding benzophenone-tetracarboxylic acid tetraester having the following formula II

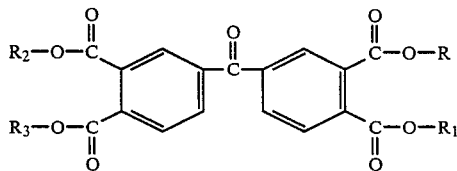

In said benzophenone-starting materials the ester forming group has the same meaning as in the benzhydrole-tetraesters and accordingly in the above stated benzophenone-tetracarboxylic acid tetraesters of formula II the radicals R, R₁, R₂ and R₃ have the same meaning as in formula I stated above.

The reduction reaction is preferably performed using a corresponding metal hydride, for instance sodiumborhydride, in a solvent, for instance an alkanol, for performing said reduction reaction.

The plastic component which is plastified according to the present invention with the stated benzhydrol-tetracarboxylic acid tetraesters is usually a hydrophobic plastic material. Preferably the plastic component accordingly is a polyethylene, a polypropylene, a polyvinylhalide, a polystyrene, a polyester, a polyamide, a polyacrylonitrile, a polymethacrylonitrile, a polyurethane, a polycarbonate, a polyvinylidenehalide, a relatively hydrophobic cellulose derivative or a copolymeric material comprising two or more monomeric units. Corresponding copolymeric materials optionally can comprise also minor quantities of monomeric units which have stronger hydrophilic properties, like e.g. monomeric units which have as substituents hydroxy groups, lower aliphatic ethers or ester groups and eventually carboxylic acid groups. Examples of the monomeric units which have higher hydrophilic properties are the corresponding monomeric units which are derived from vinyl alcohol, acrylic acid, methacrylic acid or vinyl acetate.

In the monomeric units of corresponding polymeric materials there furthermore can be present any hydrophobic substituents, like e.g. alkyl groups bonded to the phenyl nucleus of a corresponding polystyrene. Accordingly also monomeric units derived from vinyl toluene can be present in the corresponding polymeric material.

In the corresponding polymeric material there can be also present unsaturated groups and accordingly in the corresponding polymer material optionally alkine groups or alkene groups are present. This is e.g. true if the corresponding polymeric material had been prepared using a diene as monomeric constituent, like e.g. butadiene.

Preferred plastic components of the inventive plastic materials are vinylhalogenide-homopolymers and-copolymers and vinylidene halogenide-homopolymers and-copolymers like e.g. the corresponding bromides or fluorides. Specially preferred, however, are the corresponding chlorides.

According to a preferred embodiment of the present invention the plastic component of the plastic material containing as plasticizer the benzhydrol-tetracarboxylic acid tetraester is a vinylchloride homopolymer or a vinylchloride copolymer.

The inventive plastic material containing the plasticizer is preferably a shaped body. Special examples for such shaped bodies are those which have the shape of a bloc, a rod, a plate, a foil, a film, a fibre, a strand or a filament.

Preferably the inventive plastic material contains per 10 parts by weight of the plastic component at least one part by weight of the benzhydroltetracarboxylic acid tetraester.

If, however, corresponding shaped bodies will be prepared which have a high elasticity and high adhesive properties, then they will comprise per 10 parts by weight of the plastic materials 9 parts by weight to 90 parts by weight of the benzhydrol-tetracarboxylic acid tetraester, preferably the highly elastic and tacky shaped bodies contain per 10 parts by weight of the plastic component 12–90 parts by weight of the benzhydrol-tetracarboxylic acid tetraester.

If the plastic component of said highly elastic shaped body having high adhesive characteristics is polyvinylchloride having per 10 parts by weight of polyvinylchloride, there are used 12–90 parts by weight, preferably 14–85 parts by weight, of said benzhydrol-tetracarboxylic acid tetraester.

Shaped bodies, the plastic component of which is a vinylchloride homopolymer or a vinylchloride copolymer, preferably contain per 10 parts by weight of said plastic material 15–80 parts by weight and specially preferred 20–70 parts by weight of the benzhydrol-tetracarboxylic acid tetraester. The corresponding shaped body will have a high elasticity and highly adhesive properties. An example of a corresponding shaped body having said properties is one which contains 30 parts by weight of polyvinylchloride and 70 parts by weight of the benzhydrol-tetracarboxylic acid tetraester.

If the inventive plastic compositions contain lower quantities of the benzhydrol-tetracarboxylic acid tetraesters, like e.g. per 10 parts by weight of the plastic component 1–7 parts by weight of said plasticizer, then said plastic compositions are plastified and can e.g. be used for preparing corresponding foils like, foils to which layers of a further material, e.g. layers of a light sensitive material are applied. Said foils, however, are not highly elastic and they also do not firmly adhere to different substrates if they are applied to it. Such highly elastic shaped bodies having high adhesive properties can be only prepared if the higher quantities of the benzhydrol-tetracarboxylic acid tetraesters are used as plasticizing agents.

Shaped bodies which contain per 10 parts by weight of the plastic material more than 90 parts by weight of the benzhydrol-tetracarboxylic acid tetraester usually do no longer have the necessary stability of their shape, at the temperature at which said shaped bodies are used. A corresponding layer of the plastified plastic material applied to a substrate adheres firmly to said substrate, but it usually begins to flow at room temperature or temperatures slightly above room temperature, like e.g. a temperature of about 40° C.

The upper limit of 90 parts by weight of the benzhydrol-tetracarboxylic acid tetraester per 10 parts by weight of the plastic material must not be exceeded keeping in mind the above considerations, if the plastic component is polyvinylchloride. Said upper limit, however, is also dependent from the plastic component present in said plastic compositions. Some plastic materials already begin to flow at room temperature or temperatures slightly above room temperature if the corresponding shaped bodies contain per 10 parts by weight of the plastic material 70–80 parts by weight of the benzhydrol-tetracarboxylic acid tetraester.

Plastic compositions which had been plasticized by adding the above stated high quantities of the benzhydrol-tetracarboxylic acid tetraesters can be adhered to a corresponding substrate by simply pressing a shaped body to said substrate. It, for instance, is possible to press a corresponding shaped body to a first substrate onto which it firmly adheres and to press thereafter onto said shaped body a second substrate so that an adherence of the first substrate onto the second substrate is achieved. Corresponding shaped bodies used for said purpose can e.g. have the shape of small cubes, of small cylinders having a low height or of plates. With such shaped bodies having high adhesive properties, for instance products, like sheets of paper, cardboard or plastic material, can be adhered to different substrates, like substrates of wood, metal, glass, painted wall or wall paper.

Shaped bodies which contain the benzhydrol-tetracarboxylic acid tetraesters as plasticizer in such high quantities that they are highly elastic and have high adhesive characteristics have preferably the shape of threads, filaments, rods, elastic foils or elastic sheets. Corresponding highly elastic and adhesive foils and sheets can be prepared by casting a solution containing the plastic material and the benzhydrol-tetracarboxylic acid tetraester dissolved in a corresponding solvent onto a substrate and then removing of so formed sheet after the solvent had been evaporated.

Applying such solvent casting techniques which are well known to a person experienced in the art, for example there can be prepared from a solution of 10 parts by weight of polyvinylchloride and 30 parts by weight of the benzhydrol-tetracarboxylic acid tetraester in a sufficient quantity of a corresponding solvent, for example tetrahydrofurane, a shaped body in the form of a foil. According to said method foils having a thickness of 3 $\mu$m to 200 $\mu$m can be prepared. Said polyvinylchloride foils are very tacky and have high adhesive properties on different substrates, like e.g substrates which contain silicon, like glass or silicone resins, and also on substrates of plastic materials like e.g. substrates of poly(-methylmethacrylate) or polyvinylchloride.

The corresponding shaped bodies which have the shape of sheets or foils, furthermore, have a high elasticity and advantageous mechanic properties, specially a high tensile strength or breaking resistance. The corresponding highly elastic and adhesive foils can be applied in the not extended state to a substrate and thereby a good adherence is achieved. It furthermore is also possible to apply the corresponding elastic foils onto the substrate while said foils are in an extended condition. In this case the elasticity of the foil, i.e. the resiliency or the restoring forces of the extended foil, further improve the adherence of said foils onto the substrate. Independently whether the foil is applied to the substrate in the stretched or extended condition or in the not stretched condition a permanent adherence of said foil onto the substrate is achieved.

It furthermore is possible to dissolve the plastic component and the benzhydrol-tetracarboxylic acid tetraester in a solvent, preferably a volatile organic solvent and to apply said solution onto the substrate. For instance the solution can be applied onto the substrate by painting it onto the substrate, by spraying it onto the substrate or by casting it onto the substrate. After the volatile solvent is evaporated there remains on the surface of the substrate a firmly adhering layer of the highly elastic plastic material.

The foils containing the inventive plasticizers or corresponding films of the inventive plastic compositions, which had been applied to the substrate using a solvent, can be used for several packaging purposes. If such films or foils come into direct contact with an aqueous medium, for instance with a humid or liquid food product, then it is specially advantageous that the corresponding plasticizer is not eluted from the plastic foil even after long storage periods and accordingly the corresponding food product is in no way contaminated by the corresponding plasticizer.

Foils of plastic compositions which are elastic and have high adhesive properties due to the before mentioned high contents of the benzhydrol-tetracarboxylic acid tetraester, can also be used for adhering a not adhesive material onto a not adhesive substrate, like e.g. a substrate of glass, paper or plastic material. According to said procedure to the corresponding substrate there is first applied a not adhesive material, like e.g. a foil of paper or plastic material. After said foil of the not adhesive material had been laid onto the substrate an area of the inventive highly adhesive foil is applied over said not adhesive material, which area of the adhesive foil has to be greater than the area of the not adhesive material. Eventually highly elastic adhesive foils can be also applied in a slightly stretched condition. According to said procedure in the surface regions where the adhesive foils directly contact the surface of the substrate, said foils adhere firmly to the substrate. In those regions where there is the not adhesive sheet material interposed between the substrate and the adhesive foil, the adhesive foil presses the not adhesive sheet material onto the substrate. Accordingly the not adhesive sheet material is firmly adhered to the substrate through the superposed layer of the highly elastic adhesive foil. The not adhesive sheet material can e.g. be a corresponding printed sheet or a sheet having handwritten remarks so that in a single step the product in question is designated and packaged.

Inventive plastic compositions which contain the benzhydrol-tetracarboxylic acid tetraester in such high amounts that the corresponding compositions are highly elastic and have good adhesive properties, are preferably applied to substrates of the following materials:

substrates of plastic material, like e.g. poly(methylmethacrylate) or poly(vinylchloride), or substrates which contain silicon, for example substrates of glass, quartz-glass, silanized glass, substrates of doted single crystals of silicon which were coated with silicon dioxide having the formula $SiO_2$ or which were coated with silicon nitride having the formula $Si_3N_4$ as well as substrates of silicone-material like e.g. silicone resins. The inventive plastic compositions which were elastified and made adherent with high quantities of the benzhydrol-tetracarboxylic acid tetraester, have a very good adherence on all of said substrates. Corresponding firmly adhering layers can be applied either by pressing a corresponding foil of the plastic material onto the substrate in question or by applying to the substrate a layer of a solution of the plastic material and the benzhydrol-tetracarboxylic acid tetraester in a corresponding volatile organic solvent and in this case the corresponding firmly adhering layer is formed when the solvent is evaporated.

As already outlined before, when prior art plasticizers like dicarboxylic acid diesters were used, problems were encountered which were caused by a migration of the plasticizer in the matrix of the plastic material. Said problems are specially severe if rather high quantities of the plasticizer are used, as it is usual in several fields of the application, like e.g. ion selective members, for instance ion selective membranes, are made which contain as plastic material a plasticizer and an ion sensitive component.

Tests were made and it was found out that the benzhydrol-tetracarboxylic acid tetraester used in the inventive plastic compositions as plasticizers have a highly reduced migration in the matrix of the plastic material compared with prior art plasticizers like diesters of dicarboxylic acids, as for instance the corresponding esters of the phthalic acid, the sebacic acid and the adipic acid, and also compared with prior art plasticizers which are esters of the phophoric acid and, furthermore, also with regard to prior art plasticizers which are ether plasticizers like e.g. the o-nitrophenyloctylether.

Due to the inhibited migration of the benzhydrol-tetracarboxylic acid tetraesters in the matrix of the plastic material also the migration of said plasticizer into a liquid medium or a solid material which is kept in contact with said plastic composition, is inhibited. Accordingly, contrary to prior art plasticizers the inventive benzhydrol-tetracarboxylic acid tetraester-plasticizers are not eluted from the corresponding plastic compositions if said plastic compositions are contacted with different solvents, like e.g. organic aqueous solvent systems, for instance aqueous solvents which contain proteinous materials.

Corresponding tests were made with inventive membranes containing 30 parts by weight of polyvinylchloride plus 70 parts by weight of the benzhydrol-tetracarboxylic acid tetraester of formula I stated before, in which each of the radicals R, $R_1$, $R_2$ and $R_3$ was an n-octyl radical. Furthermore membranes for comparison were prepared which contained 30 parts by weight of polyvinylchloride and furthermore 70 parts by weight of the dioctylester of the sebacid acid.

Accordingly in the inventive membranes the alcohol component of the corresponding tetracarboxylic acid tetraester was identical with the alcohol component of the prior art plasticizer, i.e. the dicarboxylic acid diester plasticizer of the membranes for comparison. The inventive membranes and the membranes for comparison were immersed during several days in a solution of albumin. After said treatment, from the inventive membranes practically no plasticizer had been eluted by said albumin solution while, contrary to this, from the membranes for comparison nearly 90% of the originally present plasticizer had been eluted by the albumin solution.

In all fields of application where a plastified plastic material comes in contact with any liquid material, it is extremely important that the plasticizer of the plastic composition is not eluted by said liquid medium. Such a contact for instance occurs when corresponding plastic compositions are contacted with aqueous solutions, for instance if corresponding foils or films of plastic materials, like highly elastic foils are used for packaging purposes. Foils or films of the inventive plastic materials are advantageous if any humid products like humid food stuffs or beverages are packaged.

Furthermore, shaped bodies of the inventive plastic compositions which contain the benzhydrol-tetracarboxylic acid tetraester-plasticizer and which have the shape of threads, strands, fibres or filaments are advantageous if used in such fields of application where they come into contact with liquid media like e.g. aqueous media.

If the inventive plastic compositions are used for packaging purposes then it is advantageous in some fields of application to apply a solution containing the plastic component and the benzhydrol-tetracarboxylic acid tetraester in a volatile solvent directly to the substrate which has to be packaged. If corresponding compositions having high contents of the stated tetracarboxylic acid tetraester plasticizer are applied then there remains on the substrate, after the solvent had been evaporated, a firmly adhering layer of the plastic elastic material. Also in said field of application the fact that the plasticizer is not eluted from the plastic composition is of outstanding importance.

It was furthermore found out that the tetracarboxylic acid tetraester plasticizer used in the inventive plastic composition is not only itself firmly anchored in the matrix of the plastic material but it, furthermore, also inhibits the migration of a further component present in said plastic composition, provided that the further component does not have a very low molecular weight. Accordingly, the migration of further components present in the plastic composition which have a molecular weight of about more than 100, is inhibited by the benzhydrol-tetracarboxylic acid tetraesters.

According to a further preferred embodiment the inventive plastic material is a plastic composition which comprises in addition to the plastic component and the tetracarboxylic acid tetraester-plasticizer at least one further component having a molecular weight of more than 100 and in said plastic compositions the migration of said further component, having a molecular weight of more than 100, in the matrix of the plastic component is inhibited by the benzhydrol-tetracarboxylic acid tetraester present in said compositions.

Due to the fact that the benzhydrol-tetracarboxylic acid tetraesters inhibit also the migration of further components of not too low molecular weight in the matrix of the plastic material, also the migration of said further component into a liquid material or solid material kept in contact with the plastic material, is prevented. Said property is very important in all fields of application where the corresponding plastic material containing a further component is kept in contact with liquid materials, like aqueous solutions, and with regard to this we refer to the corresponding explanations given with regard to the elution of a plasticizer from a corresponding plastic material.

The benzhydrol-tetracarboxylic acid tetraester plasticizer, however, also inhibits the migration of extraneous materials having a not too low molecular weight into the matrix of the plastic material. Accordingly, if in the above stated fields of application an inventive plastic material is contacted with a liquid material containing dissolved therein several components having a molecular weight of about more than 100, then a migration of said components into the plastic composition is prevented through the benzhydrol-tetracarboxylic acid tetraester.

According to a further preferred embodiment of the invention the inventive plastic material is a shaped body which has applied to at least one surface of said shaped body a layer of a further material or which shaped body is kept in intimate contact with a further solid material or liquid material and in said shaped bodies the benzhydrol-tetracarboxylic acid tetraester plasticizer of the shaped body even after long storage periods does not migrate into the applied layer, or the liquid or solid material which is kept in contact with the shaped body, and furthermore the benzhydrol-tetracarboxylic acid tetraester inhibits a migration of extraneous materials having a molecular weight of more than 100, from the layer applied to said shaped body or from the solid material or liquid material which is kept in contact with said shaped body into said shaped body.

An important field of application of plastic compositions which contain a plasticizer and furthermore a third component having a molecular weight of more than 100, are ion selective members for the determination of the concentration of ions, and in said case the component having the molecular weight of more than 100, is the corresponding ion selective component.

According to a further preferred embodiment of the invention the inventive plastic composition is a corresponding ion sensitive member for the determination of the concentration of anions or cations in liquid media and the corresponding ion sensitive member contains the plastic material, the benzhydrol-tetracarboxylic acid tetraester and furthermore the ion sensitive component having a selectivity for the cation or anion to be determined, which ion sensitive component has a molecular weight of more than 100.

When the corresponding ion sensitive members are used for the determination of the concentration of anions or cations in liquid media they are brought into contact with said liquid sample solutions in which the concentrations of the anions or cations have to be determined. If such ion sensitive members are used in the clinical field of application then the sample solutions are usually body fluids, like e.g. whole blood or blood serum. Specially in said field of application prior art corresponding ion sensitive members had only a very limited period of life because corresponding prior art plasticizers, like esters of dicarboxylic acids, were eluted within short periods of time from the corresponding ion sensitive members.

In said field of application the benzhydrol-tetracarboxylic acid tetraester plasticizers are specially advantageous because they are not eluted by sample solutions during the use of corresponding ion sensitive members and because said tetracarboxylic acid tetraesters furthermore also reduce the migration of the ion sensitive component in the matrix of the polymeric material. Many ion sensitive components are known in the art and with regard to this we e.g. want to refer to the U.S. Pat. No. 2,957,607 of he applicant in which cation selective components are described. Usually the ion selective components are dicarboxylic acid amides.

In corresponding ion selective members the plasticizer is usually used in such a quantity that the ion selective component is completely dissolved in said plasticizer. Typical such membranes contain 0,1–5 parts by weight of the ion selective component, 30–40 parts by weight of the plastic component, for instance polyvinylchloride, and 60–70 parts by weight of the plasticizer.

As already explained before the rather lipophilic plasticizers used in the prior art ion sensitive membranes, like certain ethers, esters of dicarboxylic acids and esters of the phosphoric acid, were rapidly eluted from the corresponding membranes by liquid media, specially liquid media containing proteins, so that the life period of such membranes was rather limited.

Corresponding inventive ion selective membranes which contain the benzhydrol-tetracarboxylic acid tetraester-plasticizer have a far longer life period due to the inhibited migration of the plasticizer in the polymer matrix. Quite unexpectedly corresponding ion selective members, like ion selective membranes, have many further advantages when corresponding measurements are performed, compared with the corresponding prior art ion sensitive members, like e.g. shorter response time, improved reproducibility and so on.

Probably said further advantages are achieved through the better anchorage of the ion sensitive component in the polymer matrix which is achieved by the benzhydrol tetracarboxylic acid tetraester.

In the corresponding ion sensitive members the plasticizer is a benzhydrol-tetracarboxylic acid tetraester in which in the four ester groups the esterifying alcohol is selected from the group comprising alkanols, alkenols or alkinols having 4–24 carbon atoms. Preferred, however, are the previously defined preferred benzhydrol-tetracarboxylic acid tetraesters in which the corresponding alcohol moieties have 6–20 carbon atoms, and specially preferred, 9–19 carbon atoms. Furthermore, corresponding alcohol groups are preferably derived from straight chain alcohols or alcohols having an aliphatic main chain with only up to three branches. Because of said long aliphatic chains said benzhydrol-tetracarboxylic acid tetraesters and the specially preferred esters defined above, have lipophilic properties. Furthermore said long aliphatic chains lower the dynamic viscosity of said benzhydrol-tetracarboxylic acid tetraesters because of the great mass of the molecule of said substances and because of interactions between said long aliphatic chains.

It is furthermore believed that said long aliphatic chains are responsible for the drastically reduced migration of said plasticizers in the polymer matrix. It is believed that the long aliphatic chains of the tetracarboxylic acid tetraesters are positioned between the polymer chains of the polymeric component and perhaps also entanglements between long aliphatic chains of the tetraester and the long chains of the polymeric material can occur. It is furthermore believed that through such entanglements also the migration of any further components having a molecular weight of more than 100 is reduced, and accordingly also the migration of the corresponding ion selective component in the polymer matrix is strongly inhibited or nearly prevented.

Corresponding tests were performed with membranes which contain as ion selective component the N,N'-bis[(11-ethoxy-carbonyl)undecyl]N,N'-dimethyl-2,3-naphtahlindioxydiacetamide which is described in the publication of D. Amman, R. Bissig, M. Güggi, E. Pretsch, W. Simon, I. J. Borowitz and L. Weiss in Helv. Chim. Acta 58)1975) 1535. Corresponding ion selective membranes contain polyvinylchloride as plastic component and, furthermore, the preferred benzhydrol-tetracarboxylic acid tetraesters a plasticizer.

Said inventive membranes were compared with membranes for comparison which contained the same ion sensitive component in a polyvinylchloride matrix together with a prior art dicarboxylic acid diester as plasticizer, i.e. the 2-ethyl hexyl ester of the sebacic acid, i.e. the bis(2-ethyl hexyl)sebacinate.

The corresponding inventive ion sensitive membranes and also the corresponding membranes for comparison contain 30 parts by weight of polyvinylchloride and furthermore 70 parts by weight of the plasticizer.

Ion sensitive electrodes were equipped with the corresponding inventive ion sensitive membranes and with the corresponding ion sensitive membranes for comparison.

The tests showed that the life period of the electrodes equipped with the inventive ion sensitive membrane was under the same working conditions about the tenfold of the electrodes which were equipped with the membranes which contained the prior art plasticizer, i.e. the bis(2-ethyl hexyl)-sebacinate. Preferred inventive membranes which have high elasticity and high adhesive characteristics contain the following components:

10 parts by weight of polyvinylchloride,
15-90 parts by weight of the benzhydrol-tetracarboxylic acid tetraester and
0,1-1 parts by weight of the ion selective component.

The fact that in inventive ion selective members the migration or the mobility of the ion selective component is hindered through the benzhydrol-tetracarboxylic acid tetraester, is specially important when corresponding miniaturized systems are used for testing different kinds of ions in a sample solution. In said miniaturized systems ion sensitive areas which are sensitive for different kinds of ions are situated in the neighbourhood of each other. One disadvantage of corresponding prior art systems was a contamination of the corresponding ion sensitive region with the ion sensitive component of the neighbouring region. In said prior art miniaturized equipments a diffusion of the ion sensitive component of one region into the neighbouring region occurred. In the corresponding inventive plastic compositions the mobility of the ion sensitive component in the different regions of the membrane is inhibited through the benzhydrol-tetracarboxylic acid tetraester and so also the contamination of the neighbouring region is prevented.

It furthermore was found out that contrary to the inhibition of the mobility and the diffusion of larger molecules, like molecules having a molecular weight of more than 100, the diffusion of small molecules and ions is not inhibited through said benzhydrol-tetracarboxylic acid tetraesters. Accordingly in corresponding ion sensitive members the migration of the ion sensitive component is prevented, however nevertheless small molecules like carbon dioxide, oxygen and other gases, can easily migrate and therefore corresponding ion sensitive members like ion sensitive membranes, can be used for the determination of said constituents.

Accordingly, corresponding ion sensitive membranes can be prepared which contain a polymer component, preferably polyvinylchloride, the benzhydrol-tetracarboxylic acid tetraester-plasticizer and furthermore a component which enables the determination of carbon dioxide. Such components are described in the publication of J. W. Ross, J. H. Riseman and J. A. Krüger in Pure Appl. Chem. 36 (1973) 473, entitled "Potentiometric gas sensing electrodes". It is furthermore possible to prepare corresponding ion sensitive members of sensors which have an ion selectivity and also a high permeability for gases. Corresponding membrane systems are described in the publication of U. Oesch, E. Malinowska and W. Simon, entitled "Bicarbonate-selective electrodes based on planar thin membrane technology", Analytical Chemistry 59, page 2131 and following, 1986. In corresponding ion sensitive membrane systems the carbon dioxide diffuses through the ion sensitive membrane, sufficiently rapid, so that said anion can be determinated in aqueous systems. Tests were performed which showed that the benzhydrol-tetracarboxylic acid tetraester contained in the corresponding inventive ion sensitive membranes did not influence the speed of the diffusion of the carbon dioxide compared with corresponding membranes containing prior art plasticizers. The same is also true for oxygen and other gases. Accordingly, corresponding inventive membranes which contain a corresponding ion sensitive component, which is suited for the determination of said gases, in a polymer matrix, together with the benzhydrol-tetracarboxylic acid tetraester-plasticizer (or a high quantity of said benzhydrol-tetracarboxylic tetraester which acts as elasticifying component) can be used for the determination of said gases, for instance for a determination of oxygen in body fluids like e.g. blood serum.

A further advantage of such inventive ion sensitive membranes which contain so large amounts of the benzhydrol-tetracarboxylic acid tetraester that the corresponding membranes are highly elastic and have highly adhesive properties is, that said membranes can be easily applied to the body of corresponding electrodes, like electrodes of glass or silanized galss, and that after the membranes had been applied, they are adhering firmly to the electrode body. Said highly elastic membranes are not removed from the electrode body by rubbing with a finger. Furthermore when said electrodes are contacted with liquid media when they are used for the determination of the concentration of cations or anions in said liquid media, then the membrane remains firmly adhered to the electrode body when it is brought into contact with the liquid medium.

The following preparations I and II illustrate processes for preparing preferred benzhydrol-tetracarboxylic ester plasticizers which correspond to the following formula I

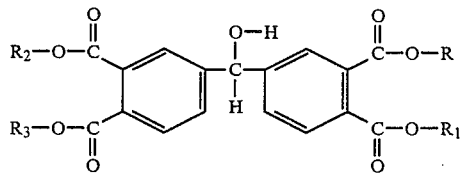

and the non limitative examples will illustrate inventive plastic compositions which contain said benzhydrol-tetracarboxylic acid tetraesters of formula I as plasticizer.

PREPARATION I

Preparation of the benzhydrol-tetracarboxylic acid tetraundecyl ester

Said ester will be abbreviated in the examples as BHT-11. It corresponds to the above stated formula I and each of the radicals R, $R_1$, $R_2$ and $R_3$ has the meaning of a straight chain alkyl radical having 11 carbon atoms.

Said benzhydrol-tetracarboxylic acid ester of formula I was prepared by reducing the corresponding benzophenone starting material of formula II

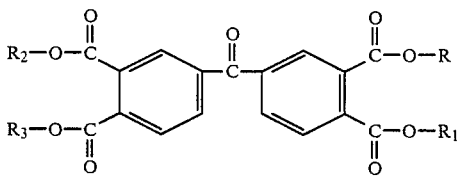

in which each of the radicals R, $R_1$, $R_2$ and $R_3$ was an n-undecane residue.

The benzophenone tetracarboxylic ester of formula II was prepared by esterifying the 3,3′,4,4′-benzophenone-tetracarboxylic acid-dianhydride with 1-hydroxyundecane.

The chemical analysis of said starting material of formula II which has a molar weight of 974,45 and corresponds to the formula $C_{61}H_{98}O_9$ gave the following results:
calculated: C=75.11 H=10.13 found: C=75.12 H=10.13.

In the IR spectrum said starting material showed two peaks at 1730 (aryl-COO, st.) and 1670 (aryl-CO-aryl, st.).

The viscosity of said starting material at 22° C. was 902.5 cP.

95 mg (2,5 mmol) of sodium borhydride were dissolved in 10 ml of methanol and said solution was added drop by drop to a vigorously stirred solution of 2 g (2,05 mmol) of the above described benzophenone-tetracarboxylic acid tetraundecyl ester in 50 ml of methanol. The reduction was performed under a nitrogen atmosphere at room temperature. After the reaction mixture had been stirred for 2½ hours, there were added 10 ml of a 3-molar acetic acid solution and the stirring continued for a further hour. Thereafter the solvents were evaporated and the residue dissolved in 100 ml of a 0,1 molar aqueous sodium carbonate solution and thereafter the product was extracted into chloroform.

After the chloroform had been evaporated there remained 1,97 g of the corresponding crude benzhydrol-tetracarboxylic acid tetraester. Said yield of the crude product corresponds to 98% of the theoretical yield.

Said crude product was purified by flash-chromatography (35 kPa) on silicagel 60 (230–400 mesh ASTM). The eluent was a mixture of one part by volume of methyl acetate and four parts by volume of hexane.

The prepared pure BHT-11 had a melting point of 28° C. The chemical analysis of said pure product having the formula $C_{61}H_{100}O_9$ gave the following results:
calculated: C=74.96% H=10.31% found: C=74.88% H=10,43%.

The constitution of said plasticizer BHT-11 was fully confirmed by the NMR spectra (in $CDCl_3$), i.e. the $^1$H-NMR (300 MHz) and the $^{13}$C-NMR (25 MHz). It was furthermore also confirmed by the infrared spectrum (in $CDCl_3$).

PREPARATION II

Preparation of the benzhydrol-tetracarboxylic acid tetrahexyl ester

Said product corresponds to formula I and all radicals R, $R_1$, $R_2$ and $R_3$ are straight chain alkyl radicals having 6 carbon atoms.

The corresponding starting material of formula II was prepared as explained in preparation I, however as esterifying alcohol the 1-hydroxyhexane was used instead of the 1-hydroxyundecane. Also the reduction of the benzophenone-tetracarboxylic acid tetraester was performed as outlined in preparation I. It yielded the desired final product named in the title.

EXAMPLE 1

Elution of inventive plasticizers and prior art plasticizers out of the matrix of the plastic component In said example inventive foils and foils for comparison were prepared and each of said foils contained 70 parts by weight of the plasticizer, either an inventive plasticizer or a plasticizer for comparison, and furthermore 30 parts by weight of polyvinylchloride. The used polyvinylchloride was a polyvinylchloride of high molecular weight which is available from the Fluka AG, Switzerland.

The following foils were prepared:

Foil I

Said foil is an inventive foil. The plasticizer of said foil was the inventive plasticizer BHT-11, the preparation of which is explained in preparation I.

Foil II

Said foil is a foil for comparison which contained a dicarboxylic diester plasticizer, i.e. the dioctylester of the sebacic acid (dioctylsebacate). Said prior art plasticizer in the future will be abbreviated as DOS.

Foil III

Said foil is a foil for comparison. It contained the prior art plasticizer ortho-nitrophenyl-octylether. Said prior art plasticizer in the following will be abbreviated as o-NPOE.

The foils for comparison II and III contained plasticizers which are frequently used as plasticizers in ion sensitive membranes, i.e. corresponding membranes which in addition to the polymeric matrix and the plasticizer furthermore contain an ion sensitive component.

In the present example 1, however, corresponding foils were prepared which did not contain an ion selective component because only the eluability of the plasticizer from the matrix of plastic material by aqueous media was tested.

The inventive foils I and the foils for comparison II and III were introduced into an albumin solution which contained 70 g albumin per liter. The albumin solution was used in such a quantity that one part by volume of the foil was immersed in 1000 parts by volume of the albumin solution. The thickness of each of the tested foils was 100 μm and the foils immersed into the albumin solution were shaken in said solution for five days at room temperature using a corresponding shaking apparatus.

After said treatment the foils were washed with water and then the plasticizer still present in the foils was determined. The corresponding value was referred to the original quantity of plasticizer which had been present in the foil before the test.

The quantity of plasticizer which was present in the foil before the treatment with the albumin solution, was counted as 100% (i.e. the original content of 70% by weight plasticizer referred to the total weight of the foil).

After the treatment with the albumin solution in the invention foil I there were still present at least 99,5% of the originally used amount of plasticizer.

Contrary to this, in the foils for comparison II which contained the prior art plasticizer DOS there were present after the test only 70,5% of the initially used quantity of plasticizer. Still worse were the results achieved with the corresponding foil for comparison III which contained the prior art plasticizer o-NPOE. In this case, after the test, there were present only 43,9% of the originally used plasticizer.

EXAMPLE 2

Migration of a plasticizer in the matrix of the plastic component

In said example the migration of an inventive plasticizer in an inventive foil was compared with the migration of a prior art plasticizer in a foil for comparison.

The tested foils were the foil I described in example 1, i.e. a foil containing 70% by weight of the inventive plasticizer BHT-11 and 30% by weight of polyvinylchloride.

The foil for comparison was the foil II described in example 1, which foil contained 70% by weight of the prior art plasticizer DOS and 30% by weight of polyvinylchloride. In said test the inventive foils and the foils for comparison both of which had a thickness of 100 μm, were brought into contact with a far thicker tube of polyvinylchloride.

In said tests there was used a polyvinylchloride tube of the kind which is used as electrode of the catheter type for the determination of ions, for example the determination of ions in the blood, after to said catheter type electrode there had been applied a corresponding ion sensitive membrane. Such polyvinylchloride tube or polyvinylchloride tubings of the catheter type are available in the market and said tubings contain a plasticizer. The polyvinylchloride tubings to which a corresponding ion sensitive membrane had been applied are used in clinical laboratories for the determination of the concentration of ions in body fluids, like blood. An essential disadvantage of said catheter type electrodes is, that they have a rather limited period of life because the plasticizer of the polyvinylchloride tubing migrates into the ion selective membrane and also the plasticizer of the ion sensitive membrane migrates into the polyvinylchloride tubing.

The test of the present example was performed in order to examine whether the above stated problems of the mutual migration of the plasticizer can be avoided with corresponding inventive membranes which contain as plasticizer the benzhydrol-tetracarboxylic acid tetraester.

The polyvinylchloride tubing available in the market which was used for the performance of the test contained 36,6% by weight, referred to the total weight of the tubing, of the plasticizer diethylhexyl-phthalate, which thereafter will be abbreviated as DEHP, and furthermore 73,4% by weight, referred to the total weight of the tubing, of polyvinylchloride.

In said test the inventive foil I, respectively the foil for comparison II was pressed onto the polyvinylchloride tubing and after a certain time of contact the foils were again removed from the polyvinylchloride tubing and the quantity of the plasticizer which had migrated from the foil into the polyvinylchloride tubing, respectively the quantity of the plasticizer of the polyvinylchloride tubing which had migrated into the foil, was determined.

Said test showed that from the inventive foil I after a period of contact with the polyvinylchloride tubing of 9480 minutes only a very low migration of the plasticizer BHT-11 of the inventive foil into the polyvinylchloride tubing had occurred. Furthermore also only extremely small quantities of the plasticizer DEHP of the polyvinylchloride tubing had migrated into the foil I after said long period of test.

Contrary to this, with the foils for comparison II already after a period of contact of only 237 minutes a migration of the plasticizer DOS of said foil into the polyvinylchloride tubing could be determined. Furthermore after said short test period also a migration of certain amounts of the plasticizer DEHP of the polyvinylchloride tubing into the foil for comparison II could be detected

EXAMPLE 3

Testing of the adherence of inventive foils containing high amounts of the benzhydrol-tetracarboxylic acid tetraester onto several substrates In said example the adhesive properties of preferred inventive polyvinylchloride foils onto several substrates were tested. Said preferred inventive polyvinylchloride foils contained per 10 parts by weight of the plastic component polyvinylchloride, at least 12 parts by weight, and specially preferred, at least 15 parts by weight of the benzhydrol-tetracarboxylic acid tetraester. Said tests showed that those inventive foils which contain the preferred high amounts of the benzhydrol-tetracarboxylic acid tetraester have an excellent adherence to different substrates, while such inventive foils which contain less than the specially preferred amount of the benzhydrol-tetracarboxylic acid tetraester, i.e. less than 12 parts by weight of said tetracarboxylic acid tetraester per 10 parts by weight of the polyvinylchloride, do not have said excellent adherence to the different substrates.

All the foils or membranes A, B, C and D, the adherence of which was tested in the present example, however, are inventive membranes which contain the benzhydrol-tetracarboxylic acid tetraundecyl-ester, abbreviated as BHT-11, the synthesis of which is disclosed in preparation I. Said membranes either contain smaller quantities of said BHT-11 as plasticizer for said plastic compositions or very high quantities of said BHT-11 as elastifying component which provides the corresponding foils with the high adhesive properties.

The membranes were prepared by dissolving the necessary quantities of polyvinylchloride and BHT-11 in a sufficient amount of tetrahydrofurane to dissolve both components. Said solution was then cast to membranes having a thickness of about 100 μm.

In the following table the parts by weight of polyvinylchloride referred to 100 parts by weight of the membrane and the parts by weight of BHT-11 referred to 100 parts by weight of the membrane, are stated for each of the foils A, B, C and D.

| foil | parts by weight of polyvinylchloride | parts by weight of BHT-11 |
|------|--------------------------------------|---------------------------|
| A    | 10                                   | 90                        |
| B    | 30                                   | 70                        |
| C    | 40                                   | 60                        |
| D    | 54                                   | 46                        |

Each of the foils A, B, C and D was tested as to its adherence on substrates of glass, silicon dioxide (quartz glass) and methyl-methacrylate (Plexiglas). The corresponding foils were applied to the corresponding substrates in a slightly extended, respectively stretched state.

All the tested foils adhered to the three substrates after they had been applied. If, however, thereafter there was rubbed with the finger over the area where the foils had been applied, then through said treatment the foils A, B and C were not peeled off, while the foil D was peeled off of all the three substrates through said treatment. All the foils A, B, C and D could be scratched off of all the substrates using a knife.

The inventive foil D stated in the table contained per 10 parts by weight of polyvinylchloride less than 12 parts by weight of the BHT-11, i.e. it contained per 10 parts by weight of the polyvinylchloride only 8,5 parts by weight of the BHT-11. Said foil, accordingly, contained less than the lower limit of the preferred shaped bodies having high elasticity and high adhesive characteristics as defined in claim 14. Through said lower content of the benzhydrol-tetracarboxylic acid tetraester said foils D did no longer have the extremely high adherence on different substrates.

The foils A, B, C and D were also tested as to their breaking strength and in these tests the results of the foils B the best.

EXAMPLE 4

Inventive plastic compositions which will not have a high elasticity and high adhesive properties contained per 10 parts by weight of the plastic component less than 9 parts by weight of the benzhydrol-tetracarboxylic acid tetraester-plasticizers. Said plastic composition for instance contained per 10 parts by weight of the plastic component 1-7 parts by weight of the benzhydrol-tetracarboxylic acid tetraester.

The corresponding inventive plastic compositions are preferably used in such fields of application where a good anchoring of the plasticizer in the matrix of plastic material is of great importance. Corresponding shaped bodies, like foils, sheets or ribbons, are advantageously used as carrier material for layers of a different material. Accordingly, to at least one side of such a foil of plastic material, there can be applied a further layer, for instance a layer of a light sensitive material. In said field of application the plastic component of the inventive plastic compositions is preferably of polyester and in said field of application it is important that a migration of components of the applied layer into the carrier of plastic materials is avoided and that furthermore also a migration of the plasticizer of the plastic composition into the applied layer is strictly avoided.

What is claimed is:

1. A plastic material containing a benzhydrol-tetracarboxylic acid tetraester as a plasticizer wherein migration of said tetraester-plasticizer in the plastic material is inhibited and migration of the tetraester-plasticizer from the plastic material into solid or liquid materials which contact the plastic material is avoided, and wherein the carboxylate group of said tetraester-plasticizer is bonded directly to the aromatic nuclei of the benzhydrol group of said tetraester-plasticizer, and wherein the esterifying alcohol moiety of said tetraester-plasticizer is selected from the group consisting of alkanols having 4-24 carbon atoms, alkenols having 4-24 carbon atoms and alkinols having 4-24 carbon atoms.

2. A plastic material as claimed in claim 1 wherein the plasticizer is a benzhydrol-tetracarboxylic acid tetraester in which the alcohol moieties of said tetraester are derived from straight chain alcohols or from alcohols having not more than three branchings.

3. A plastic material as claimed in claim 1 wherein in the benzhydrol-tetracarboxylic acid tetraester each of the two phenyl nuclei is substituted with two ester groups and wherein in the two phenyl nuclei the position of the ester groups with regard to the carbon atom of the phenyl nucleus to which the group of formula

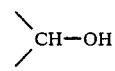

of the benzhydrol is bonded, is identical.

4. A plastic material as claimed in claim 3, wherein the benzhydrol-tetracarboxylic acid tetraester has the following formula I

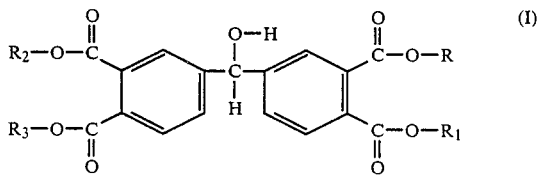

wherein each of the radicals R, $R_1$, $R_2$ and $R_3$ is selected from the group consisting of alkyl radicals having 4-22 carbon atoms, alkenyl radicals having 4-22 carbon atoms and alkynyl radicals having 4-22 carbon atoms.

5. A plastic material as claimed in claim 4 wherein in the benzhydrol-tetracarboxylic acid tetraester of formula I each of the radicals R, $R_1$, $R_2$ and $R_3$ is selected from the group consisting of alkyl radicals having 6-20 carbon atoms, alkenyl radicals having 6-20 carbon atoms and alkynyl radicals having 6-20 carbon atoms, and wherein the radicals R, $R_1$, $R_2$ and $R_3$ are straight chain radicals or radicals having not more than three branchings.

6. A plastic material as claimed in claim 1 wherein in the tetracarboxylic acid plasticizer the four ester groups have the same structure.

7. A plastic material as claimed in claim 4 wherein in the tetracarboxylic acid plasticizer the four ester groups have the same structure.

8. A plastic material as claimed in claim 1 wherein the plastic component of the plasticized composition is a polyethylene, a polypropylene, a polyvinylhalide, a polystyrene, a polyester, a polyamide, a polyacrylonitrile, a polyurethane, a polycarbonate, a polyvinylidenehalide or a copolymeric material comprising two or more monomeric units.

9. A plastic material as claimed in claim 4 wherein the plastic component of the plasticized composition is a polyethylene, a polypropylene, a polyvinylhalide, a polystyrene, a polyester, a polyamide, a polyacrylonitrile, a polyurethane, a polycarbonate, a polyvinylidenehalide or a copolymeric material comprising two or more monomeric units.

10. A plastic material as claimed in claim 1 which is a plastic composition which comprises in addition to the plastic component and the tetracarboxylic acid tetraester-plasticizer at least one further component having a molecular weight of more than 100 and wherein the benzhydrol-tetracarboxylic acid tetraester inhibits the migration of the further component having a molecular weight of more than 100 in the matrix of the plastic component.

11. A plastic material as claimed in claim 1 which comprises per 10 parts by weight of the plastic component at least one part by weight of the benzhydrol-tetracarboxylic acid tetraester.

12. A plastic material as claimed in claim 1 which is a shaped body.

13. A plastic material as claimed in claim 12 wherein to at least one surface of said shaped body there is applied a layer of a further material, and wherein the benzhydrol-tetracarboxylic acid tetraester plasticizer of the shaped body does not migrate into the applied layer, and which benzhydrol-tetracarboxylic acid tetraester furthermore inhibits migration of extraneous materials having a molecular weight of more than 100, from the applied layer into said shaped body.

14. A plastic material as claimed in claim 12 which is a shaped body, which shaped body is elastic and adhesive and contains, per 10 parts by weight of the plastic material, 9-90 parts by weight of the benzhydrol-tetracarboxylic acid tetraester.

15. A plastic material as claimed in claim 14 which shaped body contains, per 10 parts by weight of the plastic material, 12-90 parts by weight of the benzhydrol-tetracarboxylic acid tetraester.

16. A plastic material as claimed in claim 10 for the determination of the concentration of anions or cations in liquid media which contains as a further component having a molecular weight of more than 100, an ion selective component.

17. A plastic material as claimed in claim 16 which comprises an ion selective membrane, which ion selective membrane is adhesive and elastic and contains 10 parts by weight of polyvinylchloride, 15-90 parts by weight of the benzhydrol-tetracarboxylic acid tetraester and 0.1-1 parts by weight of the ion selective component.

18. A plastic material according to claim 1 wherein the aromatic nuclei of the benzhydrol group of said tetraester are substituted with nonionic substituents.

19. A plastic material according to claim 1 wherein the alcohol moieties of said tetraester are substituted with nonionic substituents.

20. A plastic material according to claim 12 wherein the shaped body has the shape of a block, a rod, a plate, a foil, a film, a fibre, a strand or a filament.

21. A plastic material according to claim 12 wherein said shaped body is kept in intimate contact with a further solid material or liquid material, and wherein the benzhydrol-tetracarboxylic acid tetraester plasticizer of the shaped body does not migrate into said liquid or solid material, and wherein said benzhydrol-tetracarboxylic acid tetraester furthermore inhibits migration of extraneous materials having a molecular weight of more than 100, from said solid material or liquid material into said shaped body.

* * * * *